United States Patent [19]
Fujiwara et al.

[11] Patent Number: 5,595,742
[45] Date of Patent: Jan. 21, 1997

[54] ANTIMICROBIAL AGENT FOR STAPHYLOCOCCUS

[75] Inventors: Hiroshi Fujiwara, Kokubunji; Ken Sawai, Osaka, both of Japan

[73] Assignee: Toyo Seiyaku Kabushiki Kaisha, Osaka, Japan

[21] Appl. No.: 351,571

[22] Filed: Dec. 5, 1994

Related U.S. Application Data

[63] Continuation of Ser. No. 9,609, Jan. 27, 1993, abandoned.

[30] Foreign Application Priority Data

Oct. 6, 1992 [JP] Japan ................................. 4-267556

[51] Int. Cl.⁶ ................................................ A61K 35/84
[52] U.S. Cl. ........................................ 424/195.1; 424/93.5
[58] Field of Search ................................. 424/93 Q, 93.5, 424/195.1; 435/115

[56] References Cited

U.S. PATENT DOCUMENTS

| | | | |
|---|---|---|---|
| 4,145,415 | 3/1979 | Sato | 424/195 |
| 4,713,331 | 12/1987 | Michel et al. | 435/68 |
| 5,221,289 | 6/1993 | Miyamatsu et al. | 8/646 |

FOREIGN PATENT DOCUMENTS

| | | | |
|---|---|---|---|
| 2368958 | 5/1978 | France . | |
| 62-195333 | 8/1987 | Japan | 35/84 |
| 63-27416 | 2/1988 | Japan . | |
| 63-316734 | 12/1988 | Japan | 35/84 |
| 0232026 | 2/1990 | Japan | 35/84 |
| 63-278414 | 5/1990 | Japan . | |

OTHER PUBLICATIONS

Cano et al, Essentials of Microbiology, West Publishing Company, New York, (1988), pp. 395 & 397.
Biological Abstracts, xol. 96, No. 1 1993, Philadelphia, PA, US;abstract no. 8225 M. A. B. Coletto et al. 'Antibiotic activity in Basidiomycetes: V. Antibiotic activity of mycelia and cultural filtrates' p. AB–919; *abstract* & Allionia (Turin): 30(0):61–64, 1990–1991.
Brock et al, Biology of Microorganisms 4th Ed., Prentice–Hall Inc: New Jersey, 1984, p. 228.

*Primary Examiner*—David M. Naff
*Assistant Examiner*—Jean C. Witz
*Attorney, Agent, or Firm*— Jordan and Hamburg

[57] ABSTRACT

An antimicrobial agent for Staphylococcus comprising an extract of the pileus of *Ganoderma lucidum*, thereby treating and preventing various infections and inflammations caused by Staphylococcus including Methicillin Resistant *Staphylococcus aureus*.

19 Claims, No Drawings

ANTIMICROBIAL AGENT FOR STAPHYLOCOCCUS

This application is a continuation of application Ser. No. 08/009,609, filed Jan. 27, 1993 now abandoned.

BACKGROUND OF THE INVENTION

The present invention concerns an efficacious antimicrobial agent for bacteria of genus Staphylococcus (hereinafter referred to as Staphylococcus) which has pathogenicity for human beings, domestic or wild animals and pets. The antimicrobial agent of the present invention is effective for various infections and inflammations of human beings and animals caused by Staphylococcus such as pyogenic dermatitis, conjunctivitis, sinusitis, otitis, cystitis, pneumonia, myelitis, arthritis, visceral abscess. The agent is also effective against Methicillin Resistant *Staphylococcus aureus* (hereinafter referred to as MRSA), being a serious problem as a pathogen of nosocomial infections.

Staphylococcus, especially *Staphylococcus aureus*, are important pathogenic bacteria concerning infections, inflammations and pyosis of human beings and animals. They also produce an enterotoxin which reacts as a pathogen of food poisoning. Recently, MRSA having resistance to many kind of antibiotics, has raised serious problems in case of nosocomial infections or grave enteritis caused by microbial selection and substitution. Since MRSA shows resistance to almost all antibiotics used practically such as penicillin and methicillin, it infects, for example, postoperative patients with reduced resistance and causes intractable pyosis and inflammation.

Therefore, valid antimicrobial agents were long sought to be developed so as to overcome the damage of Staphylococcus especially of MRSA, a notable agent, however, has yet to be seen for proper usage.

SUMMARY OF THE INVENTION

Accordingly it is an object of the present invention to provide an effective antimicrobial agent for bacteria of genus Staphylococcus. Another object of the invention is to provide an effective antimicrobial agent for *Staphylococcus aureus*, especially for MRSA.

A further object of the invention is to provide a method for treating and preventing various infections and inflammations caused by Staphylococcus, especially by MRSA. Other and further objects of the present invention will become obvious upon an understanding of the illustrative embodiments about to be described or will be indicated in the appended claims, and various advantages not referred to herein will occur to one skilled in the art upon employment of the invention in practice.

DESCRIPTION OF THE PREFERRED EMBODIMENTS

The present inventors have been investigating in various manners to find an effective antimicrobial agent for Staphylococcus, especially for *Staphylococcus aureus* and MRSA and it results in finding an extract of the pileus of fruit body of *Ganoderma lucidum* has an excellent inhibition effect of the growth of Staphylococcus, especially MRSA.

It is known that *Ganoderma lucidum* was first found in China and has been utilized as a herb medicine during the last 2000 years. In recent years various studies for the herb have been made concerning clinical effect, chemical component analysis and pharmacological effect and the herb is applied to diseases such as angina pectoris, hyperlipemia, acute viral hepatitis and leukopenia.

In view of foregoing situations, the present inventors have tried to develop an effective antimicrobial agent for Staphylococcus using *Ganoderma lucidum*, which has not yet been studied so much.

The antimicrobial agent for Staphylococcus according to the present invention has a feature in that it comprises an extract of the pileus of *Ganoderma lucidum*. More preferably, the extract is the extract of ripe pileus with many spores. Among fruit body of *Ganoderma lucidum*, pileus has more excellent inhibition effect than other parts.

A method for preparing the extract is not restricted in the present invention, and various known methods can be applied. For example, the antimicrobial agent of the present invention may be prepared by extracting the crushed pileus of *Ganoderma lucidum* with hot water for several hours, so as to obtain maximum concentration, and spray drying. Thus, powder of the extract is obtained. The powder is, for example, used as a powder drug itself or dissolved in aqueous solvent and used as a pharmaceutical solution.

The antimicrobial agent of the present invention can be applied widely to bacteria of genus Staphylococcus, such as *Staphylococcus epidermidis*, *Staphylococcus saprophyticus*, *Staphylococcus aureus* including MRSA and the like.

There is no particular restriction for the administration form. The formulations for oral administration illustratively include tablets, pills, granules, soft and hard capsules, dispersions, fine granules, powders, emulsions, suspensions, syrups, elixirs and the like. The formulation for parenteral administration include, for example, ointments, lotions, tonics, sprays, suspensions, oils, emulsions, suppositories and the like. For the formulation of the effective ingredient of the present invention, routine methods should be followed, employing appropriately surfactants, excipients, coloring agents, flavorings, sweetening agents, preservatives, stabilizers, buffers, suspending agents, isotonic agents, vitamin K, vitamin C, vitamin E, folic acid and other routinely employed substances.

The content of the extract of the pileus of *Ganoderma lucidum* should be dosed appropriately, depending on the extent of the condition of the patient, administration form, the age and the like. The recommended dosage for external preparations for skin is within a range of 5 to 15 weight percent as the amount of the effective ingredient (powdered extract), more preferably, 7.5 to 12.5 weight percent and an appropriate amount thereof should be applied to lesions several times. Generally the dosage is within 5 to 35 mg/kg per day as the amount of the effective ingredient per adult for oral and enthral administrations. Administration 2 to 3 times per day is recommended.

The invention will be understood more readily with reference to the following examples; however these examples are intended to illustrate the invention and are not to be construed to limit the scope of the invention.

EXAMPLE 1

(solution)

Sliced pileus of *Ganoderma lucidum* was chipped and immersed in purified water, then boiled for approximately 9 hours. Thus the extract of pileus of *Ganoderma lucidum* was obtained and the same was spray dried to result in a powder of the extract, the water content thereof was approximately 3 to 4 weight percent (hereinafter referred to as "pure powder"). The pure powder was dissolved in purified water as in Table 1 and the resulting solutions were applied to the following experiment.

Experiment (1) Test strain

The following strains were used for the experiment.

*Staphylococcus epidermidis*

*Staphylococcus saprophyticus*

*Staphylococcus aureus*

Methicillin Resistant *Staphylococcus aureus* (MRSA)

(2) Method

Above-mentioned 4 strains were inoculated into heart infusion bouillon for proliferation cultivation and drug sensitivity of each was measured in accordance with Halo-test, that is, disc agar diffusing capacity test.

Five nutrient agar mediums and five "Staphylococcus No. 110 mediums" (manufactured by Nissui & Co., registered trade mark) were used. Each strain proliferation cultured was smeared on each plate medium. Discs were cut out from filter paper ("No. 1 Filter Paper" manufactured by Toyo Filter Paper Mfg.) into 9 mm diameter, after being sterilized, they were immersed in solutions of the extract as shown in Table 1. Three piles of 5 discs of the same concentration were placed on each medium at three positions in a triangular shape, then the plate mediums were incubated in an incubator at 37° C. for 48 hours.

By measuring the width of growth inhibition zone (clear zone) using a caliper, each value of the width obtained from 10 plate mediums (five nutrient mediums and five "Staphylococcus No. 110 mediums") was averaged and the result is shown in Table 1.

TABLE 1

| | Width of growth inhibition zone (mm) | | | | | | | | |
|---|---|---|---|---|---|---|---|---|---|
| | Contents of pure powder of the extract of *Ganoderma lucidum* (wt %) | | | | | | | | |
| Strain | 0.1 | 0.25 | 0.5 | 1.0 | 2.5 | 5.0 | 7.5 | 10.0 | 12.5 |
| *Staphylococcus epidermidis* | 1.7 | 2.0 | 2.6 | 3.2 | 4.7 | 7.8 | 11.0 | 15.0 | 18.0 |
| *Staphylococcus aureus* | 1.6 | 2.0 | 2.6 | 3.2 | 4.7 | 7.9 | 11.0 | 15.0 | 18.0 |
| *Staphylococcus saprophyticus* | 1.8 | 2.2 | 2.8 | 3.5 | 4.9 | 8.0 | 12.0 | 15.2 | 18.5 |
| MRSA | 1.6 | 2.0 | 2.5 | 3.2 | 4.6 | 7.7 | 10.8 | 14.7 | 17.8 |

As apparently shown in Table 1, the antimicrobial agent of the present invention shows a remarkable growth inhibition effect, namely, antimicrobial effect even at the concentration of 0.1 weight percent of the solution of powdered extract. Further, it shows a notable effect to MRSA which has resistance to majority of conventional antibiotics and antimicrobial agents. The growth inhibition effect of the agent of the present invention increases as the concentration of the powdered extract increases, and a conspicuous effect was obtained when above 5 weight percent of the solution was applied.

As shown in the above, the antimicrobial agent of the present invention has an excellent growth inhibition effect for Staphylococcus. The antimicrobial agent of the present invention is effective for therapy and prevention of various infections, pyosis, inflammations and food poisoning caused by Staphylococcus.

Furthermore, the agent of the present invention has also a notable antimicrobial effect for MRSA, for which scarcity of workable drugs has been known in the past. So using the antimicrobial agent of the present invention, nosocomial infections caused by MRSA can be treated and prevented.

It should also be understood that the foregoing relates to only a preferred embodiment of the invention and that it is intended to cover all changes and modifications of the example of the invention herein chosen for the purposed of the disclosure, which do not constitute departures from the spirit and scope of the invention.

What is claimed is:

1. A method for treating Staphylococcus infections in human and non-human animals comprising administering an effective amount of a composition consisting essentially of a soluble extract of *Ganoderma lucidum* prepared from the ripe pileus containing many spores.

2. The method according to claim 1, wherein said composition is administered in an amount from between about 5 to about 35 mg/kg of said extract per day.

3. The method according to claim 1, wherein said Staphylococcus bacteria is Methicillin Resistant *Staphylococcus aureus*.

4. The method according to claim 1, wherein said composition is administered intraperitoneally.

5. The method according to claim 1, wherein said composition is administered topically.

6. The method according to claim 1, wherein said composition is administered orally.

7. The method according to claim 1, wherein said composition is in a spray dried powder form.

8. The method according to claim 1, wherein said composition is dissolved in a liquid solvent prior to administration.

9. The method according to claim 5, wherein said extract is included in said composition in a concentration of 7.5 to 12.5 weight percent.

10. A method for reducing the occurrence of Staphylococcus infections in human and non-human animals comprising administering an effective amount of a composition consisting essentially of a soluble extract of *Ganoderma lucidum* prepared from the ripe pileus containing many spores for a period of time prior to exposure to Staphylococcus bacteria.

11. The method according to claim 10, wherein said Staphylococcus bacteria is Methicillin Resistant *Staphylococcus aureus*.

12. The method according to claim 10, wherein said composition is administered in an amount from between about 5 to about 35 mg/kg of said extract per day.

13. The method according to claim 10, wherein said period of time is about 2 weeks.

14. The method according to claim 10, wherein said composition is administered intraperitoneally.

15. The method according to claim 10, wherein said composition is administered topically.

16. The method according to claim 10, wherein said composition is administered orally.

17. The method according to claim 10, wherein said composition is in a spray dried powder form.

18. The method according to claim 10, wherein said composition is dissolved in a liquid solvent prior to administration.

19. The method according to claim 15, wherein said extract is included in said composition in a concentration of 7.5 to 12.5 weight percent.

* * * * *